United States Patent
Embleton et al.

(10) Patent No.: US 6,726,665 B1
(45) Date of Patent: Apr. 27, 2004

(54) OCULAR TREATMENT DEVICE

(75) Inventors: Jonathan K. Embleton, Newbury (GB); Stephen P. Jones, Glasgow (GB); Richard J. Malcolmson, Swindon (GB); Luigi G. Martini, Birkenhead (GB); Peter J. Houzego, Oakington (GB); Sarah A. Rocca, Girton (GB); Howard N. Stevens, Glasgow (GB)

(73) Assignee: Pharmacia Aktiebolag, Stockholm (SE)

( * ) Notice: Subject to any disclaimer, the term of this patent is extended or adjusted under 35 U.S.C. 154(b) by 0 days.

(21) Appl. No.: 09/394,591

(22) Filed: Sep. 13, 1999

Related U.S. Application Data

(63) Continuation of application No. 08/793,299, filed as application No. PCT/GB95/02040 on Aug. 30, 1995, now Pat. No. 6,425,888.

(30) Foreign Application Priority Data

Aug. 30, 1994 (GB) ............................................. 9417399

(51) Int. Cl.$^7$ ............................................. A61M 35/00
(52) U.S. Cl. ........................ 604/290; 604/294; 604/296
(58) Field of Search ................................. 604/290, 294, 604/295, 296, 297; 222/94, 103, 544; 206/221, 484

(56) References Cited

U.S. PATENT DOCUMENTS

| | | |
|---|---|---|
| 3,308,818 A | 3/1967 | Rutkowski |
| 3,419,007 A | 12/1968 | Love et al. |
| 3,934,585 A | 1/1976 | Maurice |
| 4,090,642 A | 5/1978 | Baker |
| 4,158,361 A | 6/1979 | Kotuby |
| 4,338,936 A | 7/1982 | Nelson |
| 4,629,456 A | 12/1986 | Edwards |
| 4,871,091 A | 10/1989 | Preziosi |
| 5,024,355 A | 6/1991 | Jouillat et al. |
| 5,094,594 A | 3/1992 | Brennan |
| 5,349,947 A | 9/1994 | Newhouse et al. |

FOREIGN PATENT DOCUMENTS

| | | |
|---|---|---|
| AU | 414 085 B | 6/1971 |
| DE | 27 17 578 B | 11/1978 |
| DE | 2717578 | 11/1978 |

(List continued on next page.)

OTHER PUBLICATIONS

Patton, Thomas et al., "ocular Bioavailability and Systematic Loss of Topically Applied Ophthalmic Drugs", American Journal of Ophthalmology 85, 1978, pp. 225–229.
Sadiq, S.A. et al., "Ophthalmic Beta Blocker", British Journal of Ophthalmology, 1996, vol. 80, pp. 532–535.
"Ophthalmic Drug Delivery Systems" (Drugs in the Pharmaceutical Sciences, vol. 58), Published in 1993 by Marcel Dekker, pp. 8–11.

*Primary Examiner*—Kim M. Lewis
(74) *Attorney, Agent, or Firm*—McDonnell Boehnen Hulbert & Berhoff

(57) ABSTRACT

A unit container for a treatment fluid comprises a sealed enclosure of which one wall section thereof is formed with at least one opening. The enclosure is pressuriseable to discharge its contents through the opening or openings, which is or are of sufficient diameter to enable the generation of a jet and/or discrete droplets of treatment fluid discharged therefrom. The one wall section is typically a flat section of the enclosure wall, and the enclosure is typically a blister pack, with the wall section at a planar base of the blister. However, the one wall section may be dome-shaped and formed with at least one opening in the top region of the dome. Containers of the invention may be provided in packages, for example in strip form or in planar arrays. Dispensing devices are described for discharging their contents in treatment.

11 Claims, 8 Drawing Sheets

FOREIGN PATENT DOCUMENTS

| | | |
|---|---|---|
| DE | 0 370 571 | 10/1993 |
| EP | 0 224 352 A1 | 6/1987 |
| FR | 2 322 060 A | 3/1977 |
| FR | 2 660 550 A | 10/1991 |
| GB | 2 242 134 A | 9/1991 |
| GB | 2 255 918 A | 11/1992 |
| WO | WO 90/13328 A | 11/1990 |
| WO | WO 93/15972 A | 8/1993 |
| WO | WO 94/03135 | 2/1994 |
| WO | WO 96/00050 | 1/1996 |

OCULAR TREATMENT DEVICE

This is a continuation of prior application Ser. No. 08/793,299, filed Aug. 11, 1997 which is a 371 of PCT/GB95/02040 filed Aug. 30, 1995.

This invention relates to ocular treatment devices, and particularly to a device of the kind which is operable to deliver to the eye treatment fluids in the form of a jet and/or small droplets.

Ophthalmic treatment fluids are commonly administered to the eye by means of eye drops or ointments. The use of eye drops has a number of disadvantages, primarily as a consequence of the difficulty with which drops are accepted by the patient. The drops are relatively large, and the instinctive blink that is provoked by the arrival of a drop on the eye severely limits the amount of or proportion of fluid that actually contacts the target area on the eye. Typically less than 10% of a 50 $\mu$l drop can be effective, the remainder being lost by drainage, either externally or through nasolacrimal drainage. Such use of expensive treatment fluids is wasteful, as well as leading to substantial uncertainty regarding the effectiveness of a treatment. Similar comments apply to the use of ointments, although levels of wastage can be reduced by careful delivery. The greater viscosity of ointments reduces their tendency to drain or be washed away.

In our International Patent Application No. PCT/GB95/01482 there are proposed various techniques for delivering treatment fluid to the eye. These employ systems in which treatment fluid is drawn from a reservoir and discharged in a controlled manner to the eye. While these techniques are useful, there are difficulties arising from the repeated use of the multi-dose nozzle. Specifically, it is difficult to maintain the sterility of the treatment fluid in a system in which doses of fluid are successively drawn from a reservoir, and passed through a re-usable nozzle without the use of preservatives. The use of preservatives has caused some concern as discussed on pages 8–11 of "Ophthalmic Drug Delivery Systems" (Drugs in the Pharmaceutical Sciences, Volume 58), published in 1993 by Marcel Dekker.

Reference is also directed to U.S. Pat. No. 3,934,585 which discloses a variety of mechanisms for delivering unit doses of treatment fluid to the human eye. The doses are held in dispensing tubes which are fitted in the mechanisms when treatment is required. The mechanisms are operative to apply compressed air to one end of a tube resulting in the discharge of treatment fluid from the other end.

It is an aim of the present invention to minimise or eliminate the need to use preservatives in ophthalmic treatment fluids without risking contamination. Thus, in a primary aspect, the present invention provides a unit container for a treatment fluid comprising a sealed enclosure of which one wall section thereof is formed with at least one opening, the enclosure being pressuriseable to discharge its contents through said at least one opening, which opening is of sufficient diameter to enable the generation of a jet and/or discrete droplets of treatment fluid discharged therefrom.

The wall section of a container according to the invention formed with the opening or openings is typically a flat section of the enclosure wall, and the enclosure is typically a blister pack, with the wall section at a planar base of the blister. However, we have found that some particular benefits arise from the adoption of a non-planar wall section in which the opening or openings are formed. More particularly, we have found that the adoption of a dome shape in the respective wall section can result in a more reliable performance of the containers in use, and facilitate certain other beneficial developments of the containers.

Thus, in preferred embodiments of the invention, a unit container for a treatment fluid comprising an enclosure of which one wall section is dome shaped and formed with at least one opening in the top region of the dome shape, the enclosure being adapted to confine a sealed volume of treatment fluid, and pressurisable to discharge the contents of the sealed volume through said at least one opening. One or more other wall sections may also define a dome shape complementary to that with the opening, which is capable of inversion into the one wall section in the discharge of the container contents.

The enclosure of a unit container of the invention can be pressurised by the application of an external force on the side of the enclosure opposite the wall section formed with the opening or openings. Where the respective wall section is substantially flat, this method of pressurising the enclosure contents can create high stresses in the wall section, and particularly around the opening or openings. In some situations, this can result in the wall section itself tearing around the opening or openings with the consequence that the discharge of the enclosure contents becomes less predictable. By locating the opening or openings at the top of a dome shape, these stresses are reduced.

Either a single opening or an array of openings may be found in the respective wall section of the container. Various arrays are possible, and a particular choice will be influenced by a number of factors. A larger number of openings will dispense treatment fluid over a larger target area. Smaller openings produce narrower jets and/or smaller drops which will be subject to greater deceleration in their passage to the target area. This may allow the use of higher pressures. A single opening can direct a jet or stream of drops accurately to a specific target area, and minimise the time taken to deliver the treatment fluid to beat the blink response. The preferred minimum opening diameter is at least 10 $\mu$m to avoid creating a spray of droplets with insufficient linear momentum to reach their target. The use of a single opening of 100 $\mu$m diameter is particularly preferred. The intention is to create droplets no smaller than say 20 $\mu$m to avoid the creation of an inhalable spray.

Another-benefit arising from the adoption of a dome shaped wall section in which the opening or openings are defined is that discharge of substantially the entire contents of the enclosure is facilitated. If the device used to pressurise the enclosure is a piston or hammer, its operative end can be shaped to complement that of the dome such that in operation the other wall sections of the enclosure, which can similarly be shaped to complement that of the dome, are inverted against the dome shaped wall section thus substantially evacuating the entire enclosure.

The wall section of the enclosure in a container of the invention may be provided with a removable cover overlaying the opening or openings, which cover is only removed just prior to the contents of the enclosure being discharged. In this way, the contents are protected from the environment until required. In an alternative arrangement the or each opening in the wall section of the enclosure is closed by a membrane adapted to rupture upon pressurisation of the enclosure. These means demonstrate how treatment fluids can be kept sterile in containers of the invention. As a consequence, the need for the use of preservatives in the contents is minimised or eliminated.

The use of a dome wall section in preferred containers of the present invention facilitates the creation of a separate sealed volume within the enclosure. In these circumstances, the removable cover overlaying the opening or openings can be dispensed with, or at least the requirements for its sealing qualities can be reduced. According to this aspect of the invention, which can of course also be applied to a container without a dome shaped wall section with the opening or openings, a dividing wall is included within the enclosure, which dividing wall separates the wall section with the opening or openings from a region within the enclosure which defines the sealed volume. The dividing wall is adapted to rupture prior to discharge of the contents from the enclosure. Conveniently, the dividing wall can be adapted to rupture upon pressurisation of the enclosure as part of the step of discharging the contents of the sealed volume through the opening or openings in the wall section. However, the dividing wall may be adapted to rupture upon the application of an external force prior to pressurisation of the enclosure. Particularly, when the container is fitted, either as an individual unit or as part of a strip for example, in a dispensing device, a mechanism can be included to apply tensile force across the container to break the dividing wall just prior to the enclosure being pressurised.

Where a container according to the invention defines a sealed volume with a dividing wall, it will be understood that this sealed volume can be formed as a individual component of the container prior to attachment of the wall section formed with the opening or openings. This feature also offers a number of particular benefits, primarily in the manufacture of packages containing a plurality of complete containers. Manufacturing these components individually means they can be separately checked for defects prior to incorporation in d package. It also facilitates the creation of packages having containers with different dosages; either different treatment fluids or different quantities of the same fluid, and also enables a plurality of individual components to be disposed under a common dome shaped wall section, whereby different treatment fluids can be kept isolated, but mixed just prior to discharge from the opening or openings.

Containers of the invention are designed to provide for the successive or simultaneous delivery of a jet or small droplets, sometimes in the form of a stream or spray, which may be diffuse or collinear. A typical range for the size of opening in the wall section of the enclosure to achieve is up to 1000 $\mu$m, preferably 20 to 200 $\mu$m. A particularly preferred size range is 100 to 150 $\mu$m. A single opening or an array of openings can be used, conveniently punched, drilled, electroformed or laser-drilled in a plastics sheet or foil defining the wall section. A metal, typically a nickel foil is preferred for electroforming.

The form of delivery that is appropriate for a particular ophthalmic treatment; ie, single or multiple openings, and the arrangement thereof, will be dictated by the need to achieve a sufficient delivery rate to beat the "blink response", with minimal adverse reaction or unpleasant sensation to the eye. Thus, if a higher quantity of fluid must be delivered, in order to ensure delivery prior to the patient blinking, and at a tolerable impact speed, multiple openings will be used instead of a single opening to achieve a sufficient overall delivery rate.

Unit containers according to the invention can be charged such that each enclosure confines a prescribed unit dose for discharge therefrom, typically no more than 10 $\mu$l. However, larger volumes such as 20, 50 or 100 $\mu$l could be required, for example for irrigation purposes. A plurality of containers may be provided in the form of a package, conveniently on a common substrate, and preferably in the form of a strip with the containers arranged sequentially therealong.

The discharge of the contents of enclosures in containers according to the invention can most simply be accomplished by provoking the collapse of the enclosure wall, against the section having the opening or openings, preferably by a mechanical system. The wall may include a reinforced region to orient its collapse. For example, the enclosure might be crushed from the side opposite the wall section by a piston, hammer or cantilever mechanism, the action of which may be dampened to control the speed of the mechanism, with sufficient impact to discharge and project the contents a predetermined minimum distance. In an alternative, the enclosure might be formed as a cylindrical chamber, with an opposite wall portion formed as a piston for movement towards the wall section to force the enclosure contents through the opening or openings.

The invention is also directed at devices for discharging a treatment fluid from the sealed enclosures of containers of the type described above. Such a device comprises a package of the containers; a mechanism for feeding the containers seriatim to a dosing station; and means for acting on the enclosure of a container at the dosing station to discharge the contents thereof. The invention also provides a manual feed device in which provision is made for individual containers or packages thereof to be fed manually to the dosing station as required. When the wall section of the container enclosure has a cover, the device can include means for its removal prior to discharge of the enclosure contents. This means may be synchronised with the feeding mechanism.

The discharge of the contents of the enclosure at the dosing station in the above device is preferably accomplished by pressure such that it is forced through the opening or openings in the respective wall section of the enclosure. However, in an alternative, an electrostatic technique can-be used, broadly of the kind described in published European Patent Specification No. 0 224 352. For this alternative, the invention provides a modified unit container in which the enclosure is not specifically pressurisable, but has a wall which includes a conductive section for connection to a source of electrical potential, whereby application of such potential generates an electrical charge in the container contents, and its discharge through said at least one opening.

In discharging devices of the invention in which the discharge of the container contents is accomplished by pressurising its enclosure, the preferred means is a physical mechanism such as a crushing unit for acting directly on the outside of the enclosure from the side opposite the wall section formed with the opening or openings. This can take the form of a piston-cylinder mechanism, and such a mechanism can also be used to move an opposite wall portion in a cylindrical enclosure of the kind described above.

Another technique that can be used to pressurise the enclosure in containers of the invention uses piezoelectric elements. Such elements enable the degree of pressurisation achieved to be accurately controlled, and can be disposed for example, against a face of the enclosure opposite the wall section, or in the form of a ring around the body of the enclosure. In either arrangement such an element can be operated selectively or repeatedly to discharge discrete droplets or a rapid sequence. The element may take the form of an ultrasonic transducer, one which is particularly suited to the generation of a spray through an array of openings in the wall section of the enclosure.

Other features can also be employed in devices according to the invention to indicate the successful delivery of a treatment fluid to its target. A light can be provided to maintain the eye open, and this could typically be white. Alternatively, a coloured system may be employed in which a different colour indicates the stage of treatment. For example, the device can be offered up to the eye showing a red light, which will switch to green only after the predetermined dose has been dispatched.

Devices according to the invention can also include a number of safety features which are already well established in dosing devices of various kinds. The number of containers in a device will of course be finite, and a dose recorder may be included to provide an indication of the number of doses remaining or delivered. A delay mechanism can also be included to prevent the inadvertent delivery of a multiple dose. In combination with the delivery signal features referred to above, this can be of significant benefit.

It will be recognised that devices according to the invention can be for personal or hand held use, or for use on a more regular basis in institutions. For whatever use, means can be provided for ensuring a proper spacing between the device and the eye to be targeted, and this can be made adjustable, particularly in the devices adapted for institutional use. In this respect, it will be noted that the mechanisms contemplated in the present invention will be well capable of discharging a jet and/or droplets substantially horizontally or vertically upwards over a minimum distance, thereby not requiring a user to arrange for the device to be operated from directly above an eye.

In addition to the containers and devices discussed above, the present invention also provides methods of generating jets and/or droplets and of treatment, using such containers and devices. The methods of treatment additionally require the targeting of generated jets and/or droplets at a respective treatment site.

The invention will now be described by way of example and with reference to the accompanying schematic drawings wherein.

Figure 1:
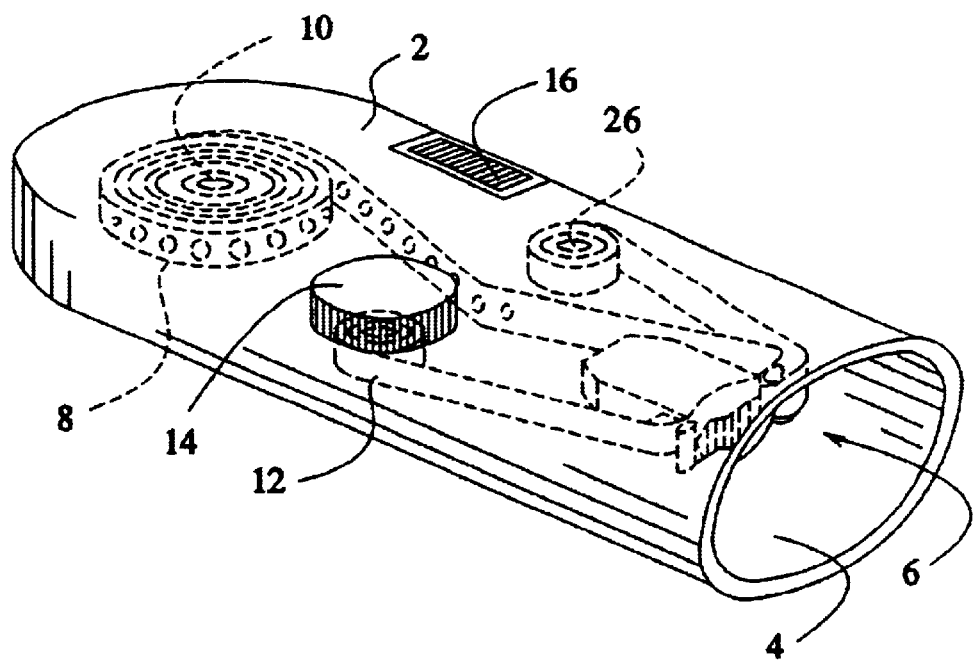
FIG. 1 is a perspective view of a device in which the enclosure of a unit is crushed to discharge its contents.

The device shown in FIG. 1 comprises a housing 2 with an open cowling 4 at one end with the dosing station 6 of the device disposed at the base thereof. The device shown is for ophthalmic treatment, and the cowling serves to ensure that the dosing station is located correctly and spaced a proper distance from the eye for a treatment to be effective. Containers according to the invention are mounted on a tape 8 which extends from a supply cord 10, around in front of the dosage station 6 and on to a take-up reel 12. A capstan 14 is provided to wind the tape on to locate a fresh container at the dosage station for discharge of its contents. A button 16 is shown for initiating the activation of the dosage station when it is properly charged.

Figure 2:
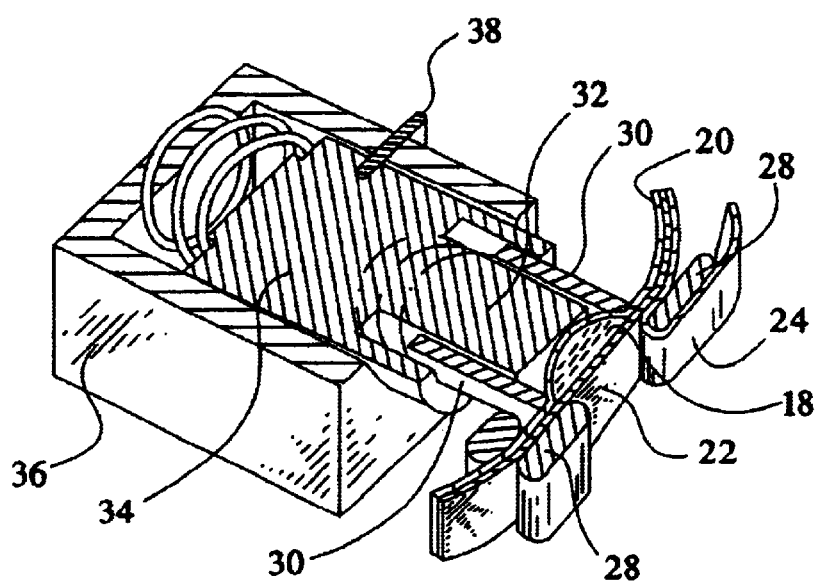
FIG. 2 is a detailed view of the crushing unit in the device of FIG. 1.

The enclosure of each container on the tape 8 takes the form of a blister pack 18 depending from a continuous backing 20, as is better shown in FIG. 2. The open face of the blister pack 18 is closed by a continuous metal foil 22, and over each blister the foil has ten 40 micron openings electroformed therein. Overlaying the foil is a cover layer 24, which is progressively removed from the foil as a blister pack reaches the dosage station 6. It is removed by a spring loaded take-up reel 26, which draws the cover layer around a guide bar 28 on the upstream side of the dosage station. A similar guide bar 28 is located on the downstream side of the dosage station, and the tape 8 is held thereagainst by means of spring loaded beams 30. These beams 30 are spaced by a distance substantially equal to the dimension of the blister 18 along the length of the tape 8 such that they also serve to locate the blister centrally at the dosage station 6.

The dosage station shown in FIG. 2 includes a piston 32 in a block 34, which is itself mounted in a housing 36 and located therein by means of a latch 38. To provoke the discharge of the contents of the blister pack 18 through the openings in the foil 22, the button 16 is depressed to release a spring (not shown) which charges the piston 32 against the blister 18, and crushes it against the foil 22. The capstan 14 is then turned to bring the next charged blister into alignment with the piston, and the capstan 14 will also be coupled to the piston 32 to retract it to its starting position prior to the fresh charged blister reaching its discharge position.

Figure 3:
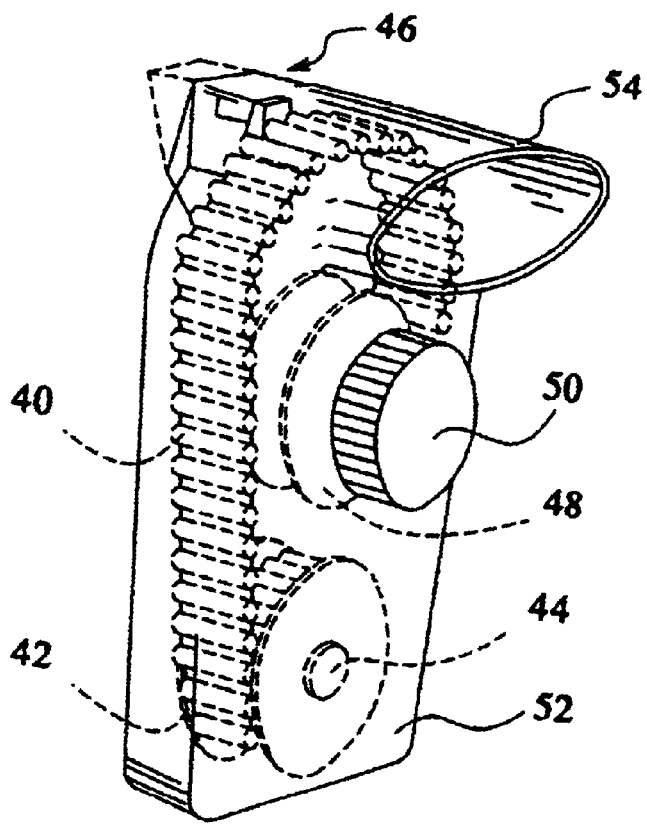
FIG. 3 is a perspective view of a device in which a piston mechanism is used to discharge the enclosure contents.

In the device shown in FIG. 3 the container enclosures 40 are mounted on a bandolier 42 which, as with the embodiment of FIG. 1, extends from a supply reel 44 past a dosage station 46 and on to a take-up reel 48 coupled to a capstan 50 for winding on. The housing 52 has a cowling 54, but it will be noted that the orientation of the housing relative to the cowling is different.

Figure 4:
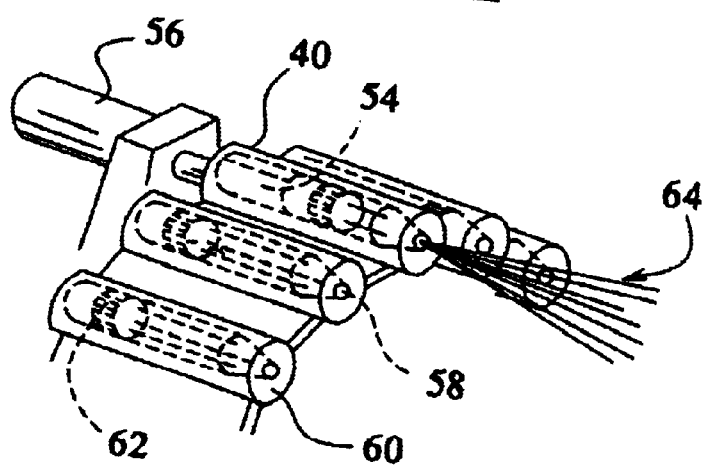
FIG. 4 is a detailed view of the piston unit of FIG. 3.

At the dosage station which is better shown in FIG. 4 each enclosure 40 is successively aligned with the piston 54 of the cylinder mechanism 56. Each enclosure 40 is cylindrical, and has at its forward end a nozzle 58 with one or a plurality of openings therein This end is closed by a foil seal 60. The other end of the enclosure 40 is closed by a silicone piston 62, and when the dosage station is activated the piston 54 engages the piston 62 and thus compresses enclosure contents. This pressure forces the contents through the opening or openings 58, simultaneously discarding the foil seal 60, and the contents are then discharged in the form of a spray as indicated at 64.

Figure 5:
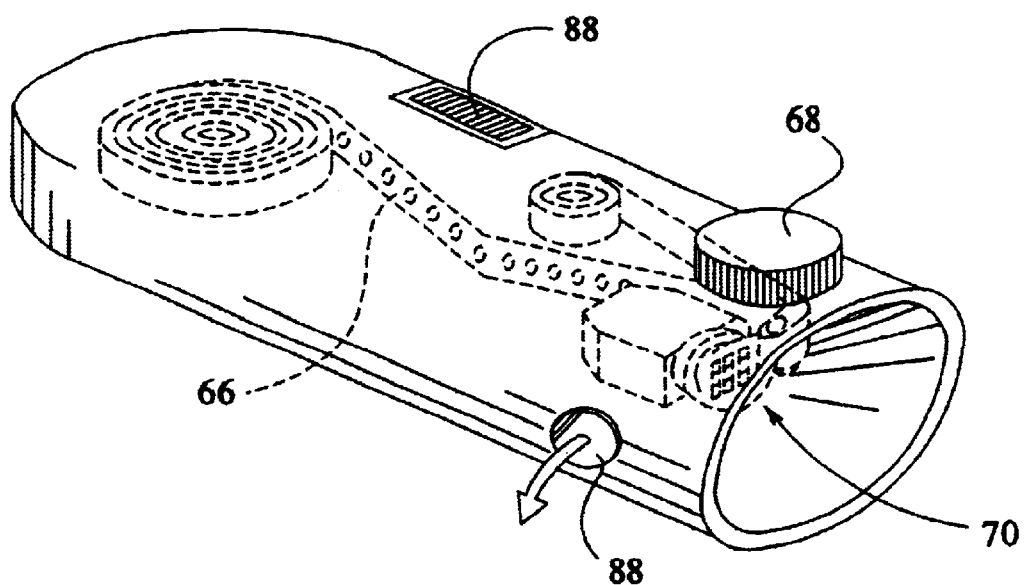
FIG. 5 is a perspective view of a device in which a piezoelectric device is used to discharge the enclosure contents.
Figure 6:
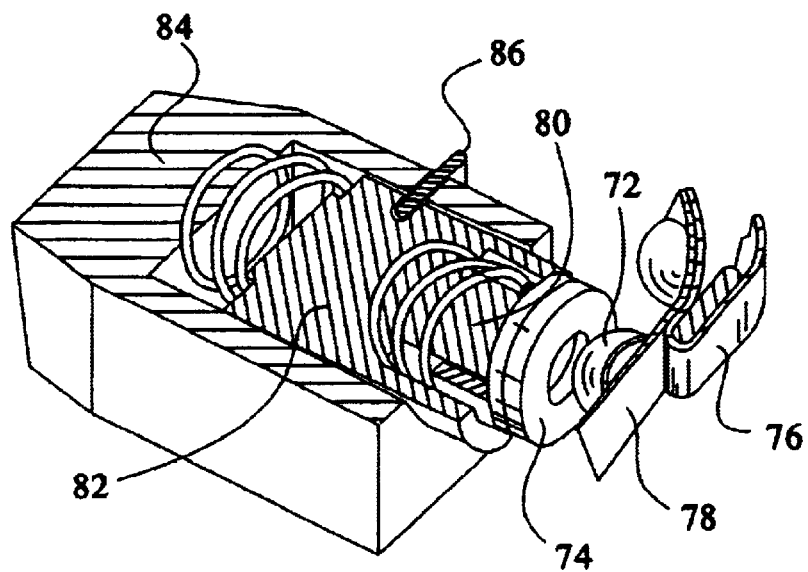
FIG. 6 is a detailed view of the piezoelectric unit of FIG. 5.

The device shown in FIGS. 5 and 6 is in some ways similar to that of FIGS. 1 and 2, but in this embodiment discharge is effected by means of a piezoelectric element. A tape 66 comprising discrete containers is wound on by means of a capstan 68 to locate a container at the dosage station 70. At the dosage station the blister 72 is aligned with a piezoelectric ring transducer 74 while a cover layer 76 is removed in substantially the same manner as it is in the embodiment of FIG. 1. Removal of the cover again exposes a metal foil 78 overlaying the blister 72 and formed with ten 40 micron electroformed openings.

As with the dosage station illustrated in FIG. 2, in this embodiment it comprises a piston 80 mounted in a cylinder 82 itself located in a housing 84 by means of a latch 86. Depression of the button 88 activates a spring to move the piston towards the blister 72, but only to locate the piezoelectric ring transducer 74 around the body thereof. Means (not shown) then activate the transducer 74 to contract it around the blister 72 and thus discharge the contents thereof through the openings in the metal foil. Again, and as described above with reference to FIGS. 1 and 2, winding the tape on with the capstan 68 also retracts the piston 80. However, in this embodiment the capstan 68 also actuates a knife to detach the used blister from the tape 66, which is then ejected through an opening 89 in the device housing.

Figure 7:
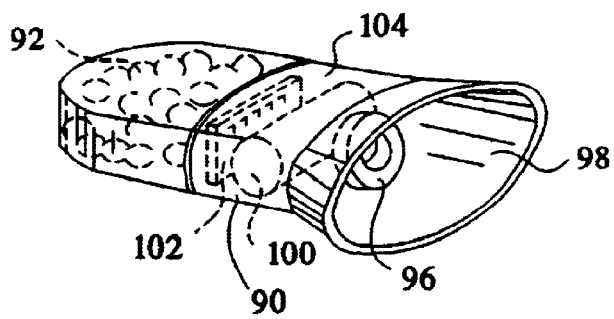
FIG. 7 is a perspective view of a device similar to that of FIGS. 5 and 6 but for use with individual containers.
Figure 8:
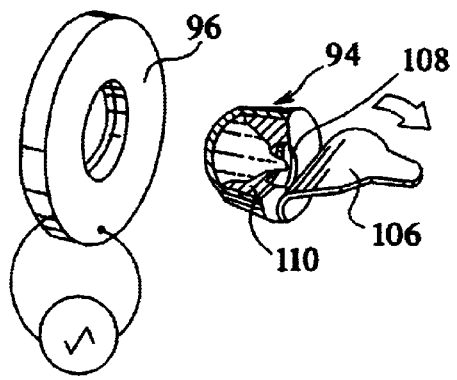
FIG. 8 is a detailed view showing a container being presented to the piezoelectric unit.

FIGS. 7 and 8 illustrate what can be regarded as a simplified version of the embodiment of FIGS. 5 and 6. In this embodiment, the containers are provided separately, and the housing 90 of the device is provided with a storage compartment 92 for the container supply. When the device is to be used, a container 94 must be removed from the storage compartment 92 and manually fitted to the ring transducer 96 fixed at the base of the cowling 98 of the housing. A battery 100 and the requisite electronics 102 are disposed in a chamber 104 located between the storage compartment 92 and the transducer 96. To use the thus charged device, a cover 106 is removed from the visible face of the container 94 to expose a wall section 108 of the enclosure formed with a 50 micron nozzle. When the electronics 102 are activated by a button (not shown) the ring transducer 96 contracts around the container 94 to discharge its contents through the nozzle.

As can be seen, the enclosure of the container 94 is reinforced around its inner perimeter by a section 110. This inhibits rupture of the enclosure upon contraction of the ring transducer, and its internal shape also serves to increase the discharge velocity of fluid from the enclosure through the nozzle.

Figure 9:
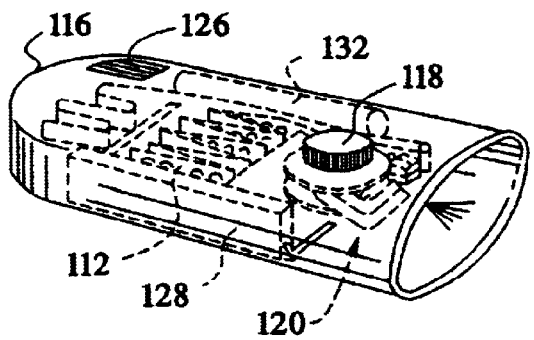
FIG. 9 is a perspective view of a device which uses an electrostatic charging system to discharge the enclosure contents.
Figure 10:
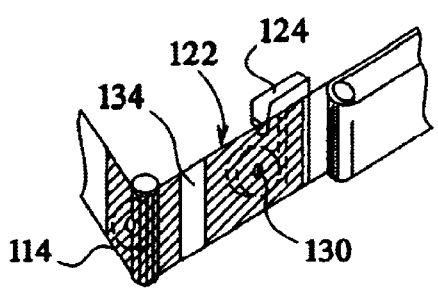
FIG. 10 is a detailed view of the dosing station of the unit of FIG. 9.

FIGS. 9 and 10 illustrate an alternative embodiment of the invention in which the contents of the enclosure are discharged by means of an electrostatic charging system. A covered strip 112 of containers 114 is provided in the housing 116, with a capstan 118 for advancing the strip 112 to locate a container 114 at the dosing station 120, broadly in the manner described with reference to FIGS. 1 and 2. In this embodiment however, the enclosures 122 of the containers 114 are formed of an electrically conductive material. A contact 124 is located at the dosing station 120 to engage the enclosure wall, and a switch (not shown), activated by the dispense button 126 is provided to apply an electrical potential from a generator 128 to the enclosure wall to charge the contents and force their discharge through the opening 130. Power for the generator 128 is provided by a battery 132, also located in the housing 116. Because the enclosure wall in each container is conductive, they must be isolated from each other in the strip 112. Thus, as shown in FIG. 10, the strip has an insulating section 134 between the containers 114.

Provision can be made for devices of the invention to deliver different fluids to a target site in a composite treatment. Thus, containers enclosing different fluids can be included for feeding to the dosing station, and where the containers are mounted on a strip or bandolier, then a chosen sequence can be predetermined. For example, an anaesthetic or diagnostic aid such as fluorescein might be enclosed in alternate containers mounted on a strip.

Figure 11:
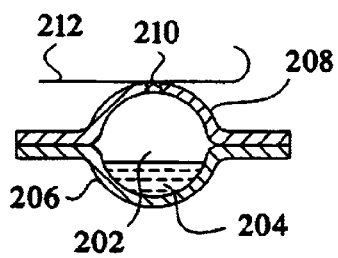
FIG. 11 is a cross-section through a preferred container according to the invention.
Figure 12A:
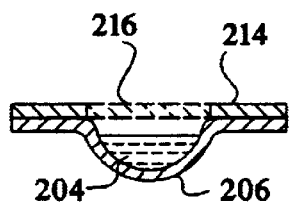
FIGS. 12A, 12B and 12C illustrate cross-sections at different stages in the manufacture of another preferred container according to the invention.
Figure 12B:
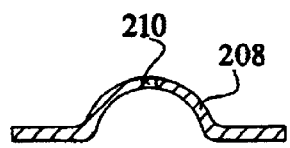
Figure 12C:
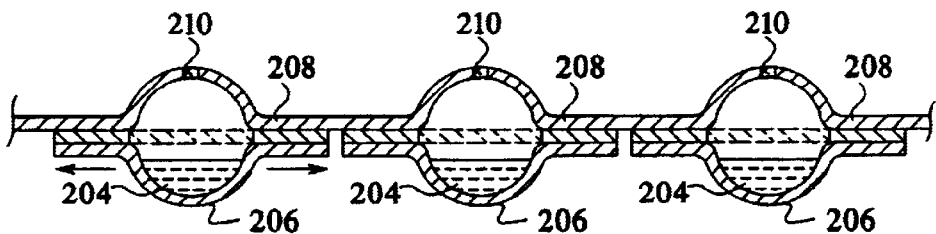
Figure 13:
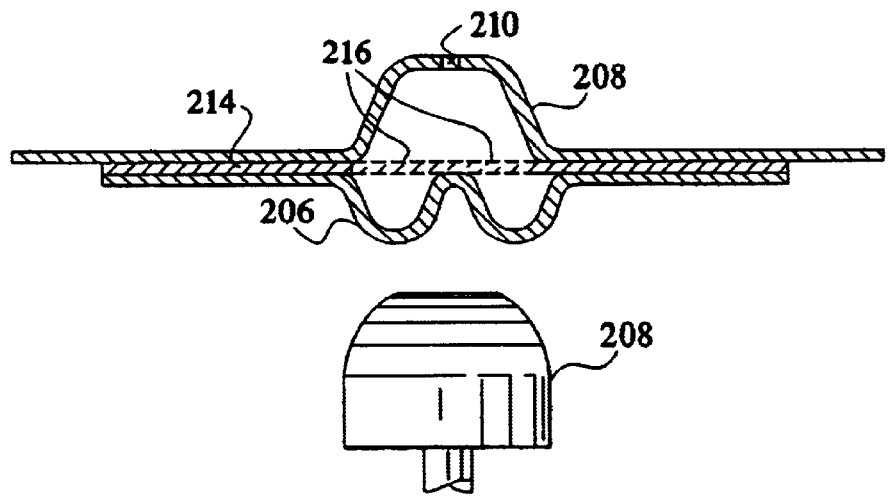
FIG. 13 illustrates yet another preferred container according to the invention.

FIGS. 11 to 13 illustrate preferred containers for use in the devices described above, which are of "double-dome" construction. The container shown in FIG. 11 defines an enclosure 202 in which is held a quantity of treatment fluid 204. The lower part of the container as shown is created as a blister in a foil laminate base sheet 206 which is overlaid with a foil laminate upper sheet 208 which is formed into a dome where it defines the upper part of the enclosure 202. The base and upper sheets 206, 208 are bonded where they contact one another to seal the enclosure at the junction therebetween.

In the top section of the upper sheet 208 is formed an opening 210, which is closed by a cover sheet 212 making sealing engagement with the external surface of the upper sheet 208 around the opening 210. The cover sheet 212 is typically a plastics sheet or a metal foil.

In use, the container shown in FIG. 11 is fitted in a device which properly locates the enclosure 202 relative to means such as a piston or air pressure source, for forcing the base sheet 206 where it forms the lower part of the enclosure 202, towards the opening 210 and against the upper sheet 208. The cover sheet 212 is removed, and the system actuated. As a consequence, the treatment fluid 204 in the enclosure 202 is discharged through the opening 210 towards its chosen target.

FIG. 12 illustrate a container in which individual components of the container can be prepared separately with treatment fluid therein, and thereafter attached to an upper sheet which completes the respective containers. Such a component is shown in FIG. 12A, which consists of a base sheet 206 formed into a blister to hold a quantity fluid 204. The blister is closed by an intermediate layer 214 sealed around the periphery of the blister to the base sheet, but including a weakened section 216 which actually overlays the blister. Nevertheless, the component illustrated is sealed, and the treatment fluid 204 in the blister is properly protected from contact with the external atmosphere. It also allows autoclave sterilisation of the sealed volume.

FIG. 12B shows a section of upper sheet 208 formed with an opening 210 for disposal over the blister of the component shown in FIG. 12. The assembled combination is shown in FIG. 12C.

Each component shown in FIG. 12A is manufactured as a discrete element, and may be subject to quality control examination to ensure that as a treatment fluid dosage component, it is sound in every particular. To complete a container from which the treatment fluid 204 may be discharged in accordance with the invention, an upper sheet 208 is laid and sealed thereover with its domed section including the opening 210 disposed directly opposite the blister in which the treatment fluid 204 is held. If a strip of containers is to be formed, then a continuous length of upper sheet 208 formed with a series of domed sections can be used to simultaneously complete and interconnect a package of containers according to the invention. Such a package is illustrated in FIG. 12C.

The use of a container of the type illustrated as part of the package of FIG. 12C is generally similar to that of FIG. 11, with two essential differences. Firstly, a cover sheet 212 is not essential because the treatment fluid 204 is already sealed within the volume defined within the container by the layer 214. Nevertheless, some form of cover sheet might still be used, although it will be understood that the bond between the cover sheet 212 and the upper sheet 208 around the holes 210 does not have to be effective to seal the enclosure to the same extent as it does in the embodiment of FIG. 11. Secondly, when the enclosure is pressurised, and particularly when the sealed volume containing the treatment fluid 204 is compressed, the first effect is the rupturing of the weakened section 216 of the layer 214, and the weakened section 216 may be designed to rupture along a defined axis. Thereafter, the discharge is essentially similar to that of the embodiment of FIG. 11. The weakened section 216 may also absorb some of the crushing force during the collapse of the blister, resulting in lower pressures and a reduced tendency of the blister or dome to burst or tear.

If because of the pressurising system used or for any other reason, there is a need to rupture the weakened section 216 prior to actual pressurisation of the enclosure, this can be accomplished. The discharge device used can be adapted such that the laminate of base and upper sheets 206, 208, and layer 214 is gripped on either side of the blister, and stretched across the blister to rupture the weakened section 216 before a piston for example, engages the base sheet 206 to collapse the enclosure. The direction of such stretching is indicated by the arrows shown adjacent the container shown on the left-hand side of FIG. 12C.

FIG. 13 shows a container in which two treatment fluids can be confined separately in the same enclosure, within respective sealed volumes closed by weakened sections of an intermediate layer 214. The manufacture, assembly and use of the container is essentially similar to those described with reference to FIG. 12, but FIG. 13 also illustrates a piston or hammer 218 for effecting discharge of the treatment fluids through the opening 210.

It will be appreciated that the shapes of the blister in the sheet 206 and the dome in the sheet 208 can be made complementary such that when a piston such as 218 is applied to the blister, or blisters as shown in FIG. 13, the entire section of sheet defining the blister or blisters eventually engages the section of sheet defining the dome to substantially completely evacuate the enclosure of the treatment fluid or fluids previously contained therein. This of course is particularly important in treatments where dosages must be accurately defined.

The separate manufacture of individual components of containers in accordance with the invention facilitates not only quality control, but also sterilisation and other preparatory procedures. In the embodiments described above, a foil laminate upper sheet 208 can be used in which only a single opening 210 is formed. However, particularly where a plurality of openings are required, the preferred material for the upper sheet 208 is a metal foil in which openings are made by photoresist electroforming. The bonding of metal foils directly to laminated base sheets can have a deleterious effect upon treatment fluid otherwise exposed in the blister. These effects are much reduced where the treatment fluid is already confined in its own sealed volume under the intermediate layer 214, and where the upper sheet is bonded to the intermediate layer 214.

In some instances it may be desirable to have a smooth discharge of treatment fluid through the opening or openings in the dome shaped wall section, or indeed the opening or openings through which fluid is discharged from any of the containers described herein. To this end preferred opening or openings should taper towards the discharge end, with the inlet diameter typically of the order of three times that of the outlet. The preferred axial length of the opening or openings is 1 to 5 times the outlet diameter, and at the outlet the opening may be made substantially cylindrical.

The terms "dome" and "dome shaped" have been used in the above description of FIGS. 11 to 13 in a very broad sense. They are not intended to define a particular or necessarily symmetric form of closure in containers of the invention. Others could be used to equivalent effect. What is however important, is the disposition of the opening or openings in the top region thereof whereby discharging fluid is directed towards the opening or openings as the enclosure is pressurised.

Figure 14:
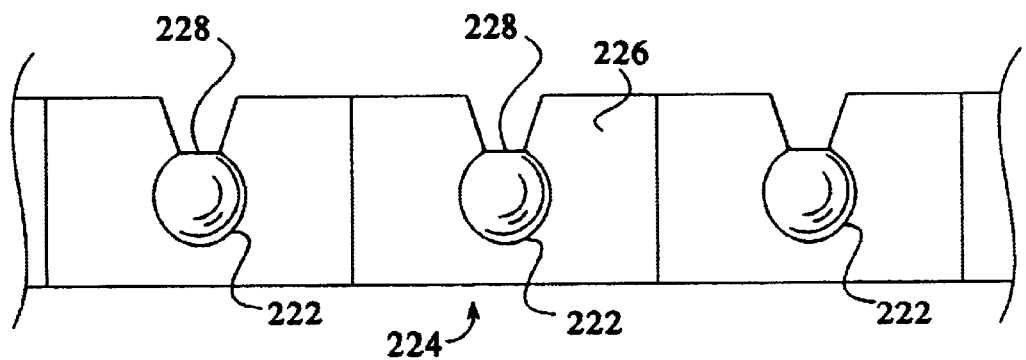
FIG. 14 shows in plan view a length of strip or bandolier formed with unit containers in the form of sachets embodying the invention.
Figure 15:
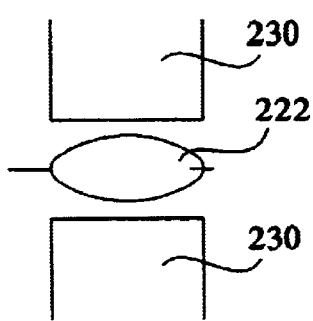
FIG. 15 illustrates a simple compression device for discharging the contents of a sachet of the type illustrated in FIG. 14.
Figure 16:
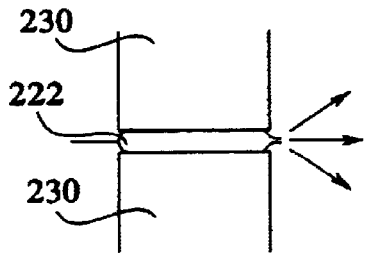
FIG. 16 shows the device of FIG. 15, having been activated to discharge the sachets contents.

In the system illustrated in FIGS. 14, 15 and 16, individual sachets 222 of treatment fluid are mounted on a strip 224. Each sachet 222 is pear-shaped, and held in the backing or support sheet 226 for use as needed. Each sachet has a weakened wall section 228 located adjacent a cut out in the support sheet 226.

In use, the strip 224 is moved in a device (not shown) to locate a sachet 224 at a discharge station. At the discharge station two opposing pistons or hammers 230 are caused to accelerate towards each other. This compresses the sachet 224 as shown in FIG. 16 to force the contents of the sachet therefrom in the direction shown. The pistons or hammers are then withdrawn, releasing the emptied sachet which is then discarded.

The weakened wall section 228 can be very small, in order to accurately focus the discharge on the chosen target. Further, it can have a line of weakness across a diameter, or alternatively an array of weak points which rupture in a pre-ordained manner.

Figure 17:
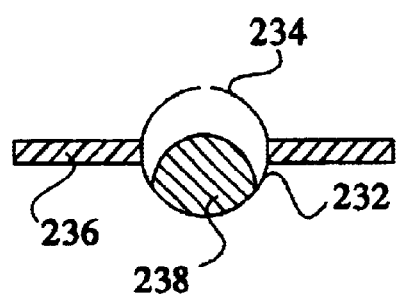
FIG. 17 shows in cross-section yet another unit dose container embodying the invention.

The container shown in FIG. 17 comprises juxtaposed sheets 232 and 234 of for example, 30 $\mu$m aluminium foil laminate and 40 $\mu$m copper foil respectively, shaped and held around a continuous path in a hot melt adhesive layer 236 to form a sealed bubble in which is confined an 8 $\mu$l unit dose 238 of a treatment fluid. Each sheet 232, 234 forms substantially half the bubble wall, and at the apex of the dome formed by the copper foil layer 234 a single 100 $\mu$m opening is made, typically by punching, drilling, electroforming or laser-drilling. The layer 236 forms flanges on either side of the bubble, and a strip of containers may be made, interconnected by a continuous length of the layer 236.

Figure 18:
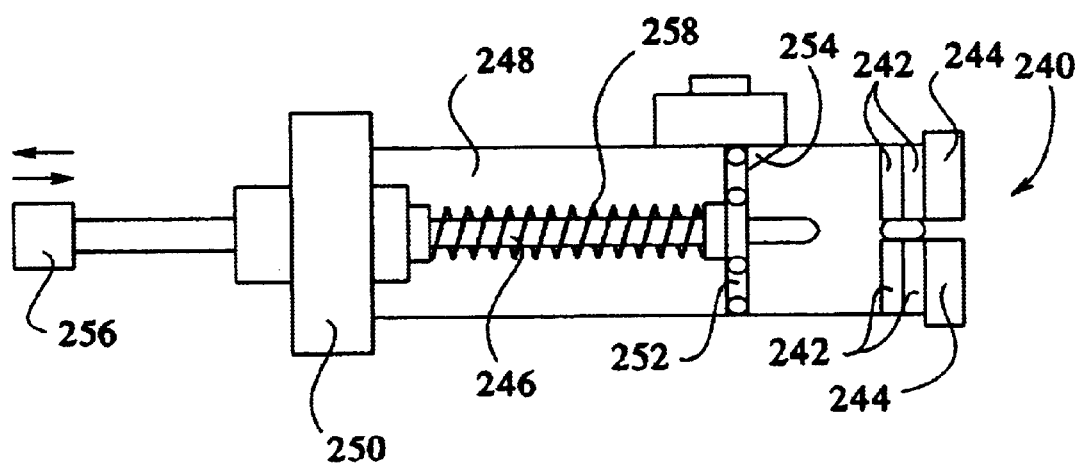
FIG. 18 shows a device for discharging the contents from a container as shown in FIG. 17.

The device shown in FIG. 18 has a dosing station 240 with two pairs of clamping plates 242 which define a path for a strip of containers of the kind illustrated in FIG. 17 with continuous flanges formed by the layer 236 disposed between respective plate pairs. When the device is ready to operate, the plates 242 clamp together to hold the flange and therefore the bubble in the appropriate position in the dosing station. The plates may be clamped by twisting the elements 244, or by an automatic mechanism activated by triggering the device.

Location of a container at the dosing station aligns it with an elongate piston 246 mounted for axial linear movement within a main housing 248. The piston 242 is principally supported in a back panel 250 mounted on the housing 248, and is guided at its forward end by a guide screw 252, to which the piston is attached. Compressed between the panel 250 and the guide screw 252 is a spring 258, and it is held compressed by a catch 254 which engages the forward face of the guide screw 252. Operating the catch 254 releases the guide screw 252 and piston 246 which is then driven by the spring 258 to engage the nearer side of the "bubble" and force the contents out of the container through the 100 $\mu$m opening. To "re-cock" the device for further use, the piston 246 is merely withdrawn to the left as shown against the force of the spring 258 until the guide screw 252 latches behind the catch 254. The guide screw 252 is balanced by a counterweight 256 at the other end of the piston 246, which can also be used to pull the piston back against the force of the spring.

The device of FIG. 18 was used in a study of the ocular response of rabbits to treatment according to the invention. The rabbits selected for the study were allowed to acclimatise for 4–5 days prior to treatment. They were subjected to manual restraining for 2 days prior to the study to condition them to the procedures involved in dosing. A device of the kind illustrated in FIG. 18 was then used to administer a single spray of isotonic 2% Pilocarpine hydrochloride (Pilocarpine HCl) solution to the corneal surface of the left eye of each of 5 rabbits, the right eyes remaining undosed. The following settings were used:

100 µm nozzle diameter 2.5 µm distance between nozzle tip and animal eye

Sprays targeted towards the centre of the cornea of the animal eye

The miotic response (reduction in pupil diameter) at various intervals following the application of the pilocarpine HCl solution was monitored under constant illumination using video photography. The pupil diameter of the left eye was expressed in proportion to the diameter of a fixed reference aperture situated at an equal distance from the video camera. The actual diameter was then calculated from the known diameter of the reference aperture.

Figure 19:
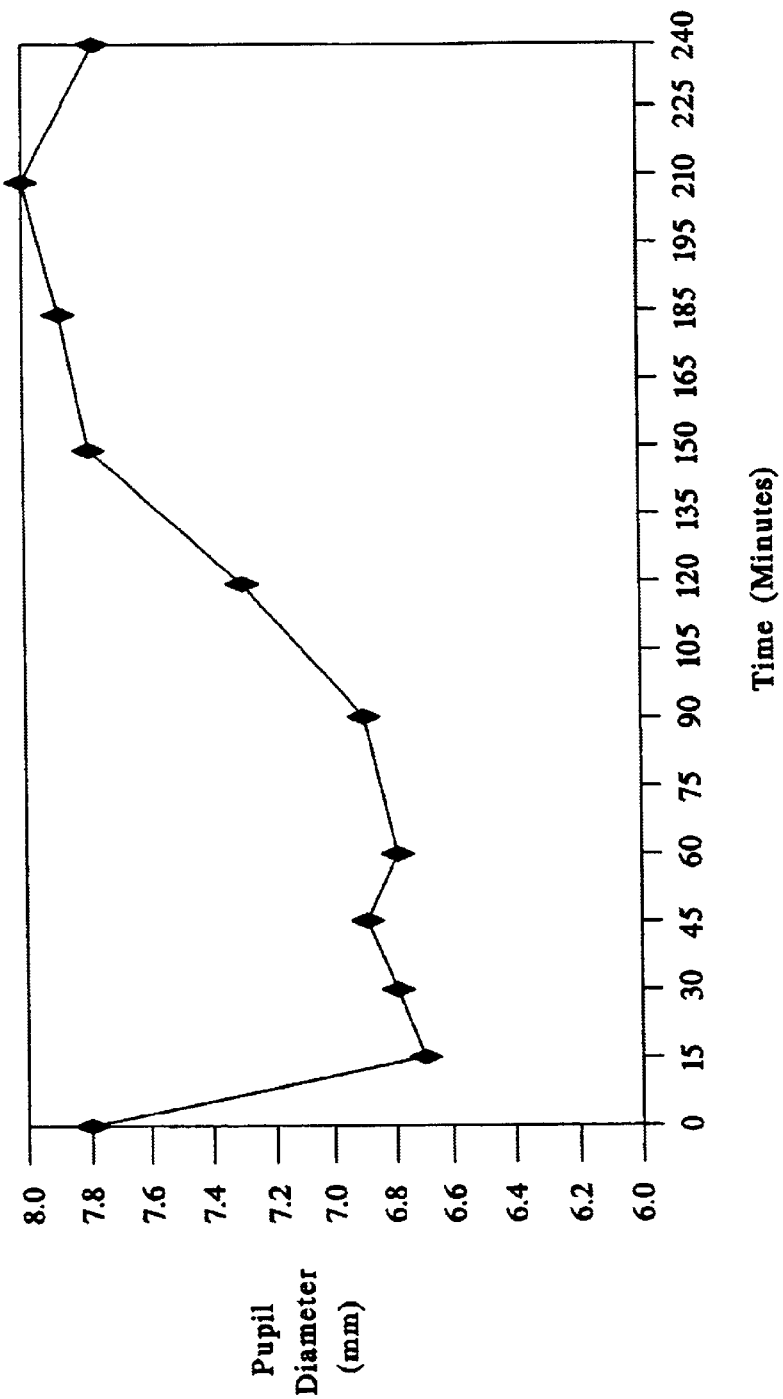
FIG. 19 is a graph showing the miotic response of rabbits subjected to treatment using the device of FIG. 18.

Table 1 shows the pupil diameter of the left eye at different intervals following application of the test dose, as is represented graphically in FIG. 19.

TABLE 1

Pupil Diameter (mm) Following Application of 2% Pilocarpine HCl Using a Laboratory Model Blister Crushing Device (Mean of 5 Rabbits)
Measurement Timepoint

| | Dose (0 min) | +15 min | +30 min | +45 min | +1 hr | +1.5 hr | +2 hr | +2.5 hr | +3 hr | +3.5 hr | +4 hr |
| --- | --- | --- | --- | --- | --- | --- | --- | --- | --- | --- | --- |
| Mean | 7.8 | 6.7 | 6.8 | 6.9 | 6.8 | 6.9 | 7.3 | 7.8 | 7.9 | 8.0 | 7.8 |

Devices according to the invention can typically generate droplets with diameters of the order of 200 µm, enabling the delivery of multiple droplets in metered doses of very low volume, 5 µl being typical. However, smaller droplets can be desirable in some applications, as can larger droplets in others. A typical delivery velocity is 10 m/s, but other velocities may be appropriate in particular applications. Because of the manner in which the dose is delivered, this provides a significant benefit over traditional treatment techniques in which large doses of say 50 µl are used. Using a device according to the invention in ocular treatment a much greater proportion of treatment liquid will actually make effective contact with the eye, leading to less wastage, reduced risk of systemic absorption and less flooding of the eye and risk of provoking blinking or watering which can result in a treatment being wasted.

Ophthalmic treatment fluids that may be used with the invention may be aqueous or non-aqueous liquids, optionally containing a therapeutic compound or compounds such as:

1) Anti-glaucoma/IOP (intra-ocular pressure) lowering compounds
   a) β-adrenoceptor antagonists, e.g. carteolol, cetamolol, betaxolol, levobunolol, metipranolol, timolol, etc.
   b) Miotics, e.g. pilocarpine, carbachol, physostigmine, etc.
   c) Sympathomimetics, e.g. adrenaline, dipivefrine, etc.
   d) Carbonic anhydrase inhibitors, e.g. acetazolamide, dorzolamide, etc.
   e) Prostaglandins, e.g. PGF-2 alpha.
2) Anti-microbial compounds (including anti-bacterials and anti-fungals), e.g. chloramphenicol, chlortetracycline, ciprofloxacin, framycetin, fusidic acid, gentamicin, neomycin, norfloxacin, ofloxacin, polymyxin, propamidine, tetracycline, tobramycin, quinolines, etc.
3) Anti-viral compounds, e.g. acyclovir, cidofovir, idoxuridine, interferons, etc.
4) Aldose reductase inhibitors, e.g. tolrestat, etc.
5) Anti-inflammatory and/or anti-allergy conpounds, e.g. steroidal compounds such as betamethasone, clobetasone, dexamethasone, fluorometholone, hydrocortisone, prednisolone etc. and non-steroidal compounds such as antazoline, bromfenac, diclofenac, indomethacin, lodoxamide, saprofen, sodium cromoglycate, etc.
6) Artificial tear/dry eye therapies, comfort drops, irrigation fluids, etc., e.g. physiological saline, water, or oils; all optionally containing polymeric compounds such as acetylcysteine, hydroxyethylcellulose, hydroxymellose, hyaluronic acid, polyvinyl alcohol, polyacrylic acid derivatives, etc.
7) Diagnostics, e.g. fluorescein, rose bengal, etc.
8) Local anaethetics, e.g. amethocaine, lignocaine, oxbuprocaine, proxymetacaine, etc.
9) Compounds which assist healing of corneal surface defects, e.g. cyclosporine, diclofenac, urogastrone and growth factors such as epidermal growth factor, etc.
10) Mydriatics and cycloplegics e.g. atropine, cyclopentolate, homatropine, hysocine, tropicamide, etc.
11) Compounds for the treatment of pterygium, such as mitomycin C, collagenase inhibitors (e.g. batimastat) etc.
12) Compounds for the treatment of macular degeneration and/or diabetic retinopathy and/or cataract prevention.
13) Compounds for systemic effects following absorption into the bloodstream after ocular administration, e.g. insulin.

The above compounds may be in the form of free acids or bases or alternately as salts of these. Combinations of compounds e.g. an anti-bacterial combined with an anti-flammatory may be desirable for the optimization of therapy in some instances. The compounds may be formulated as aqueous or non-aqueous (e.g. oil) solutions or suspensions. Formulations may optionally contain other formulation excipients, for example, thickening agents such as gels, mucoadhesives and polymers, stabilisers, anti-oxidants, preservatives, pH/tonicity adjusters etc.

It will be appreciated that devices of the invention might comprise a single unit, as well as the modular systems illustrated in which the delivery mechanism and the treatment liquid source are provided separately, or at least independent of each other. Modular systems do of course enable a fluid or treatment liquid to be selected, and coupled to a delivery mechanism as desired. This enables the same delivery mechanism to be used for different treatments. Such a device of the invention for institutional use can provide for such selection to be at least partially automated.

What is claimed is:

1. An ocular treatment device for discharge of a treatment liquid from a sealed enclosure of a container having
   a) a first wall section;
   b) at least one opening arranged in the first wall section, said opening having a minimum diameter of at least 10 micrometers;
   c) a second wall section arranged opposite the first wall section, the first wall section and the second wall section forming an enclosure confining a sealed unit dose volume of the liquid, the device comprising:
      i) a housing,
      ii) a dosing station for the enclosure arranged in the housing,
      iii) a crushing unit operative to compress the container enclosure at the dosing station to discharge the contents of the enclosure therefrom, and
      iv) a cowling arranged on the housing and adapted for ensuring a proper spacing between the dosing station and eye to be targeted with the treatment liquid.

2. The device in claim 1 wherein the crushing unit comprises a mechanical system.

3. The device in claim 1 wherein the crushing unit comprises a piston, hammer or cantilever mechanism arranged for impact on the enclosure.

4. The device in claim 3 wherein the crushing unit is dampened to control the speed thereof.

5. The device of claim 3 wherein the enclosure first wall section is dome shaped and the crushing unit operative end is shaped to complement that of the dome.

6. The devices of claim 1 wherein the crushing unit is arranged for urging the second wall structure towards the first wall structure.

7. The device of claim 1 including means for feeding the containers seriatim to the dosing station.

8. The device of claim 7 wherein a plurality of said containers are connected by a common supporting substrate.

9. The device of claim 8 wherein the feeding means is manually operable.

10. The device of claim 7 wherein each container has a removable cover overlaying said at least one opening, the device including means for removing the cover of a said container prior to discharge of its contents.

11. The device of claim 10 wherein the removing means operates synchronously with the feeding mechanism.

* * * * *